US007012064B2

(12) United States Patent
Or et al.

(10) Patent No.: US 7,012,064 B2
(45) Date of Patent: *Mar. 14, 2006

(54) CYCLOSPORINS FOR THE TREATMENT OF IMMUNE DISORDERS

(75) Inventors: Yat Sun Or, Watertown, MA (US); Tsvetelina Lazarova, Brookline, MA (US); Jens Werner Eckstein, Arlington, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 359 days.

This patent is subject to a terminal disclaimer.

(21) Appl. No.: 10/349,890

(22) Filed: Jan. 23, 2003

(65) Prior Publication Data

US 2003/0186855 A1    Oct. 2, 2003

Related U.S. Application Data

(63) Continuation-in-part of application No. 09/800,856, filed on Mar. 5, 2001, now Pat. No. 6,784,156.

(51) Int. Cl.
*A61K 45/00* (2006.01)
*A61K 47/00* (2006.01)

(52) U.S. Cl. ................. 514/11; 514/2; 514/9; 530/317; 530/402; 530/321

(58) Field of Classification Search ............... 514/2, 514/11, 9; 530/321, 317, 402
See application file for complete search history.

(56) References Cited

U.S. PATENT DOCUMENTS

| 4,554,351 | A | 11/1985 | Wenger | 544/177 |
|---|---|---|---|---|
| 4,798,823 | A | 1/1989 | Witzel | 514/11 |
| 5,239,057 | A | 8/1993 | Wang et al. | 530/321 |
| 5,427,960 | A | 6/1995 | Wang et al. | 436/536 |
| 5,643,870 | A | 7/1997 | Boelsterli et al. | 514/11 |
| 5,827,706 | A | 10/1998 | Leitner et al. | 435/183 |
| 6,605,593 | B1 | 8/2003 | Naicker et al. | 514/11 |
| 2002/0132763 | A1 | 9/2002 | Naicker et al. | 514/11 |

FOREIGN PATENT DOCUMENTS

| EP | 0296122 | 12/1988 |
| WO | WO 99/18120 | 4/1999 |
| WO | WO 99/65933 | 12/1999 |

OTHER PUBLICATIONS

Billich et al., Enzymatic Synthesis of CsA, J. Biol. Chem., 262, 17258-17259 (1987).
Faulds et al., Cyclosporin: A Review of its Pharmacodynamic and Pharmacokinetic Properties, and Therapeutic Use in Immunoregulatory Disorders, Drugs 46, 953-1040 (1993).

*Primary Examiner*—Jon Weber
*Assistant Examiner*—Samuel Wei Liu
(74) *Attorney, Agent, or Firm*—Edwards Angell Palmer & Dodge LLP; Jeffrey D. Hsi

(57) ABSTRACT

The present invention relates to methods of treating or preventing an inflammatory or immune disorder in a subject while eliminating or reducing the toxicity associated with the administration of cyclosporin A, comprising systemically administering to said subject a pharmaceutical composition comprising a therapeutically effective amount of at least one compound of Formula (I) or a pharmaceutically acceptable salt, ester or prodrug thereof, in combination with a pharmaceutically acceptable carrier or excipient:

(I)

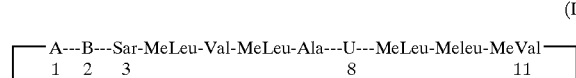

in Formula (I), the formula for residue A is:

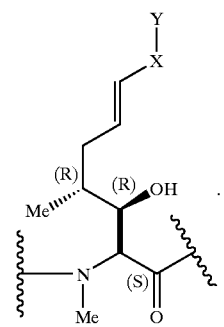

4 Claims, No Drawings

CYCLOSPORINS FOR THE TREATMENT OF IMMUNE DISORDERS

This application is a continuation-in-part of application Ser. No. 09/800,856, filed Mar. 5, 2001 now U.S. Pat. No. 6,784,156.

TECHNICAL FIELD

The present invention relates to methods of treating or preventing an inflammatory or immune disorder in a subject through the systemic administration of a therapeutic amount of at least one cyclosporin analog or pharmaceutically acceptable salts, esters, or prodrugs thereof.

BACKGROUND OF THE INVENTION

The cyclosporins comprise a class of structurally distinctive, cyclic, poly-N-methylated undecapeptides, commonly possessing pharmacological activity, in particular immuno-suppressive, anti-inflammatory or anti-parasitic activity. The first of the cyclosporins to be isolated was the naturally occurring fungal metabolite cyclosporin, Cyclosporin A represented as follows:

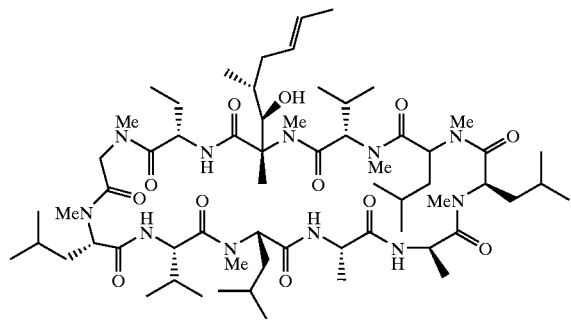

Since the original discovery of cyclosporin, a wide variety of naturally occurring cyclosporins have been isolated and identified, and many further non-natural cyclosporins have been prepared by total- or semi-synthetic means or by the application of modified culture techniques. The class comprising cyclosporins is thus now substantial and includes, for example, the naturally occurring Cyclosporins A through Z, for example, $[Thr]^2$, $[Val]^2$, $[Nva]^2$ and $[Nva]^{2-}$, $[Nva]^5$-Cyclosporin (also known as Cyclosporins C, D, G and M respectively), $[(D)MeVal]^{11}$-Cyclosporin (also known as Cyclosporin H), [cf., Traber et al.; 1, Helv. Chim. Acta, 60, 1247–1255 (1977); Traber et al.; 2, Helv. Chim. Acta, 65, 1655–1667 (1982); Kobel et al.; Europ. J. Applied Microbiology and Biotechnology, 14, 273–240 1982); and Von Wartburg et al.; Progress in Allergy, 38, 28–45, 1986)]; as well as various non-natural cyclosporin derivatives and artificial or synthetic cyclosporin derivatives and artificial or synthetic cyclosporins including dihydrocyclosporins [in which the MeBmt-residue is saturated by hydrogenation]; derivatized cyclosporins (e.g., in which the 3'-O-atom of the MeBmt-residue is acylated or a further substituent is introduced at the α-carbon atom of the sarcosyl residue at the 3-position); and cyclosporins in which variant amino acids are incorporated at specific positions within the peptide sequence, for example, $[3-O-acetyl-MeBmt]^1$-Cyclosporin (also known as Dihydro-cyclosporin D), $[(D)Ser]^8$-Cyclosporin, $[MeIle]^{11}$-Cyclosporin, $[MeAla]^6$-Cyclosporin, $[(D)Pro]^3$-Cyclosporin etc., employing the total synthetic method for the production of cyclosporins developed by R. Wenger—see e.g. Traber et al., 1; Traber et al., 2; and Kobel et al., loc cit. U.S. Pat. Nos. 4,108,985, 4,220,641, 4,288, 431, 4,554,351, 4,396,542 and 4,798,823; European Patent Publication Nos. 34,567A, 56,782A, 300,784A and 300,785; International Patent Publication No. WO 86/02080 and UK Patent Publication Nos. 2,206,119 and 2,207,678; Wenger 1, Transpl. Proc., 15 Suppl. 1:2230 (1983); Wenger 2, Angew. Chem. Int. Ed. 24 77 (1985) and Wenger 3, Progress in the Chemistry of Organic Natural Products, 50,123 (1986).

The compound cyclosporine (cyclosporine A or CsA) has found wide use since its introduction in the fields of organ transplantation and immunomodulation, and has brought about a significant increase in the success rate for transplantation procedures. Side effects with systemic CsA include increase in diastolic blood pressure, decrease in renal function, hepatic dysfunction, hypertrichosis, tremor, gingival hyperplasis, and paraesthsia. The systemic toxicity of CsA limits its use for the treatment of certain diseases. It is therefore desirable to find immunosuppresant compounds with improved systemic efficacy and safety.

SUMMARY OF THE INVENTION

The present invention relates to methods of treating or preventing an inflammatory or immune disorder in a subject while eliminating or reducing the toxicity associated with the administration of cyclosporin A, through the systemic administration of a therapeutic amount of at least one cyclosporin analog of the following Formula (I) or a pharmaceutically acceptable salt, ester, or prodrug thereof, in combination with a pharmaceutically acceptable carrier or excipient:

(I)
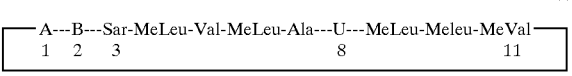

In Formula I, the formula for residue A is:

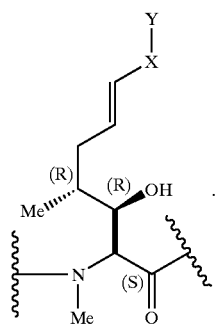

where X is absent, —$C_1$–$C_6$ alkyl-, or —$C_3$–$C_6$ cycloalkyl-; Y is selected from the groups: —C(O)—O—$R^1$; —C(O)—S—$R_1$; —C(O)—$OCH_2$—$OC(O)R^2$; —C(S)—O—$R^1$; and —C(S)—S—$R_1$; where $R^1$ is hydrogen, $C_1$–$C_6$ alkyl optionally substituted with halogen, heterocyclics, aryl, $C_1$–$C_6$ alkoxy or $C_1$–$C_6$ alkylthio or halogen substituted $C_1$–$C_6$ alkoxy, halogen substituted $C_1$–$C_6$ alkylthio and where $R^2$ is $C_1$–$C_6$ alkyl optionally substituted with halogen, $C_1$–$C_6$ alkoxy, $C_1$–$C_6$ alkylthio heterocyclics or aryl; B is -αAbu-, -Val-, -Thr- or -Nva-; and U is -(D)Ala-, -(D)Ser- or —[O-(2-hydroxyethyl)(D)Ser]-, or —[O-acyl(D)Ser]- or —[O-acyl(D)Ser]- or —[O—(2-acyloxyethyl)(D)Ser]-.

The present invention also contemplates method(s) of prevention of organ transplantation rejection and treatment of autoimmune disorders and inflammation in a subject by administering to the subject therapeutically effective amounts of the cyclosporin analogs of the present invention with or without the concurrent use of other known treatments or pharmaceutically acceptable carriers or excipients.

DETAILED DESCRIPTION OF THE INVENTION

The present invention relates to a method of preventing or treating an inflammatory or immune disorder in a subject while eliminating or reducing the toxicity associated with the administration of cyclosporin A, through the systemic administration of a therapeutically effective amount of a pharmaceutical composition comprising at lease one cyclosporin analog of the following formula (I) or a prodrug or pharmaceutically acceptable salt thereof, in combination with a pharmaceutically acceptable carrier or excipient:

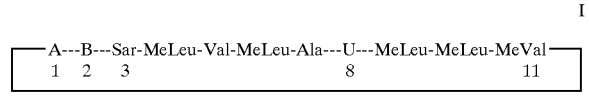

In formula I, the formula for residue A is:

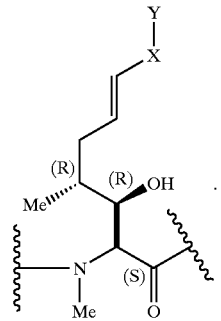

where X is absent, —$C_1$–$C_6$ alkyl-, or —$C_3$–$C_6$ cycloalkyl-; Y is selected from the groups: —C(O)—O—$R^1$ where $R^1$ is hydrogen, $C_1$–$C_6$ alkyl optionally substituted with halogen, heterocyclics, aryl, $C_1$–$C_6$ alkoxy or $C_1$–$C_6$ alkylthio, halogen substituted $C_1$–$C_6$ alkoxy or halogen substituted $C_1$–$C_6$ alkylthio; —C(O)—S—$R^1$ where $R^1$ is hydrogen, $C_1$–$C_6$ alkyl optionally substituted with halogen, heterocyclics, aryl, $C_1$–$C_6$ alkoxy or $C_1$–$C_6$ alkylthio, halogen substituted $C_1$–$C_6$ alkoxy or halogen substituted $C_1$–$C_6$ alkylthio; —C(O)—OCH$^2$—OC(O)$R^2$ where $R^2$ is $C_1$–$C_6$ alkyl optionally substituted with halogen, $C_1$–$C_6$ alkoxy, $C_1$–$C_6$ alkylthio, heterocyclics, or aryl; —C(S)—O—$R^1$ where $R^1$ is hydrogen, $C_1$–$C_6$ alkyl optionally substituted with halogen, heterocyclics, aryl, $C_1$–$C_6$ alkoxy or $C_1$–$C_6$ alkylthio, halogen substituted $C_1$–$C_6$ alkoxy or halogen substituted $C_1$–$C_6$ alkylthio; and —C(S)—S—$R^1$ where $R^1$ is hydrogen, $C_1$–$C_6$ alkyl optionally substituted with halogen, heterocyclics, aryl, $C_1$–$C_6$ alkoxy or $C_1$–$C_6$ alkylthio, halogen substituted $C_1$–$C_6$ alkoxy, halogen substituted $C_1$–$C_6$ alkylthio; B is -αAbu-, -Val-, -Thr- or -Nva-; and U is -(D)Ala-, -(D)Ser- or —[O-(2-hydroxyethyl)(D)Ser]-, or —[O-acyl(D)Ser]- or —[O-(2-acyloxyethyl)(D)Ser]-.

In Formula I, abbreviation of amino acid residues, for example, -Ala-, -MeLeu-, -αAbu-, etc., are in accordance with conventional practice and are to be understood as having the L-configuration unless otherwise indicated (for example, -(D)Ala- represents a residue having the D-configuration). Abbreviation of residues preceded by "Me-" represents a α-N-methylated amino acid residue, for example, "Me-Leu" is a α-N-methylated-Leucine residue. Individual residues of a molecule of the cyclosporin analog of the present invention are numbered, as in the art, clockwise and starting with the residue -MeBmt-, corresponding to residue 1. The same numerical sequence is employed throughout the present specification and claims.

In a preferred embodiment, the method of the present invention comprises administering to a subject a cyclosporin analog of Formula I or a pharmaceutically acceptable salt, ester, or prodrug thereof, where residue A is as previously defined, B is -αAbu-, and residue U is -(D)Ala-.

In another preferred embodiment, the method of the present invention comprises administering to a subject a cyclosporin analog of Formula I or a pharmaceutically acceptable salt, ester, or prodrug thereof, where X is absent in residue A, residue B is -αAbu- and residue U is -(D)Ala-.

The methods of treatment of the present invention are accomplished through administration of at least one cyclosporin analog, or a pharmaceutically acceptable salt ester, or prodrug thereof, which include, but are not limited to, the following compounds as illustrated below:

Compound of Formula (I) wherein B=-αAbu-, U=-(D)Ala-, X is absent, Y=COOCH$_3$,

Compound of Formula (I) wherein B=-αAbu-, U=-(D)Ala-, X is absent, Y=COOH,

Compound of Formula (I) wherein B=-αAbu-, U=-(D)Ala-, X is absent, Y=COOEt,

Compound of Formula (I) wherein B=-αAbu-, U=-(D)Ala-, X is absent, Y=COOCH$_2$CH$_2$CH$_3$, Compound of Formula (I) wherein B=-αAbu-, U=-(D)Ala-, X is absent, Y=COOCH$_2$Ph, Compound of Formula (I) wherein B=-αAbu-, U=-(D)Ala-, X is absent, Y=COOCH$_2$F, Compound of Formula (I) wherein B=-αAbu-, U=-(D)Ala-, X is absent, Y=COOCHF$_2$, Compound of Formula (I) wherein B=-αAbu-, U=-(D)Ala-, X is absent, Y=COOCF$_3$, Compound of Formula (I) wherein B=-αAbu-, U=-(D)Ala-, X is absent, Y=COOCH$_2$CF$_3$, Compound of Formula (I) wherein B=-αAbu-, U=-(D)Ala-, X is absent, Y=COOCH$_2$Cl, Compound of Formula (I) wherein B=-αAbu-, U=-(D)Ala-, X is absent, Y=COOCH$_2$OCH$_3$, Compound of Formula (I) wherein B=-αAbu-, U=-(D)Ala-, X is absent, Y=COOCH$_2$OCH$_2$CH$_2$OCH$_3$, Compound of Formula (I) wherein B=-αAbu-, U=-(D)Ala-, X is absent, Y=C(O)SCH$_2$Ph, Compound of Formula (I) wherein B=-αAbu-, U=-(D)Ala-, X is —CH$_2$CH$_2$CH$_2$, Y=COOCH$_3$, and Compound of Formula (I) wherein B=-αAbu-, U=-(D)Ala-, X is absent, Y=COOFmoc.

The compounds of Formula (I) demonstrate potent immunomodulatory activity in various common in vitro biological assays (for example, calcineurin phosphatase and binding assays, NFAT reporter gene assay, murine and human mixed lymphocyte reaction) or animal models (for example delayed-type hypersensitivity response—DTH,—allergan induced pulmonary eosinophilia) indicate that these compounds possess immunosuppressive, antimicrobial, antifungal, antiviral, antiinflammatory, and antiproliferative activity, and possess the ability to reverse chemotherapeutic drug resistance. As agents block T-cell activation, a prerequisite for HIV proliferation, the compounds are useful as prophylactics for the prevention of HIV replication. The compounds of Formula (I) would be useful when used alone, or in combination therapy with other immunosuppressants, for example, but not limited to, FK506, rapamycin, cyclosporin A, picibanil, mycophenolic acid, azathioprine, prednisolone, cyclophosphamide, brequinar and leflunomide.

As immunosuppressants, the compounds of Formula (I) are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention would also find utility in the treatment of autoimmune diseases, such as rheumatoid arthritis, systemic lupus erythematosis, hyper-immunoglobulin E, Hashimoto's thyroiditis, multiple sclerosis, progressive systemic sclerosis, myasthenia gravis, type I diabetes, uveitis, allergic encephalomyelitis, glomerulonephritis, and the like; and further infectious diseases caused by pathogenic microorganisms, such as HIV (Human Immunodeficiency Virus). In the particular cases of HIV-1, HIV-2 and related retroviral strains, inhibition of T-cell mitosis would suppress the replication of the virus, since the virus relies upon the host T-cell's proliferative functions to replicate.

Further uses include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, multiple myeloma, etc.; obstructive airway diseases, which includes conditions such as COPD, asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions would include but are not limited to ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV (Human Cytomegalovirus) infection, anti-ionflammatory activity, and so on.

The compounds of Formula (I) may be used as vaccines to treat immunosuppression in a subject. It is sometimes found that the antigen introduced into the body for the acquisition of immunity from disease also acts as an immunosuppressive agent, and therefore, antibodies are not produced by the body and immunity is not acquired. By introducing a compound of Formula (I) into the body as a vaccine, the undesired immunosuppression may be overcome and immunity acquired.

The compounds of Formula (I) may also find utility in the chemosensitization of drug resistant target cells. Cyclosporin A and FK-506 are known to be effective modulators of P-glycoprotein, a substance which binds to and inhibits the action of anticancer drugs by inhibiting P-glycoprotein, as they are capable of increasing the sensitivity of multidrug resistant (MDR) cells to chemotherapeutic agents. It is believed that the compounds of the invention may likewise be effective at overcoming resistance expressed to clinically useful antitumour drugs such as 5-fluorouracil, cisplatin, methotrexate, vincristine, vinblastine and adriamycin, colchicine and vincristine.

Further, it has recently been shown that the steroid receptor-associated heat shock proteins, hsp56 or hsp59, belong to the class of immunophilin proteins (see "HSP70 induction by cyclosporin A in cultured rat hepatocytes: effect of vitamin E succinate," Andres, David et al., *Instituto de Bioqimica, Facultad de Farmacia, Universidad Complutense, Madrid, Spain*. J. Hepatol. (2000) 33(4), 570–579; "Cyclosporin A Induces an Atypical Heat Shock Response," Paslaru, Liliana, et al., Unite de Genetique Moleculaire, Paris, Fr. Biochem. Biophys. Res. Commun. (2000), 269(2), 464–469; "The cyclosporine A-binding immunophilin CyP-40 and the FK506-binding immunophilin hsp56 bind to a common site on hsp90 and exist in independent cytosolic heterocomplexes with the untransformed glucocorticoid receptor," Owens-Grillo, Janet K. et al., Med. Sch., Univ. Michigan, Ann Arbor, Mich. USA. J. Biol. Chem. (1995), 270(35), 20479–84). The ability of a steroid receptor-associated heat shock protein to bind the immunosuppressive CsA suggests that the steroid receptor and immunophilin signal transduction pathways are functionally interrelated. The combined treatment of compounds of the present invention and low concentrations of a steroid ligand (for e.g., progesterone, dexamethasone) result in a significant enhancement of target gene expression over that seen in response to ligand alone. Thus, the compounds of Formula (I) potentiate steroid-mediated transactivation.

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

Accordingly, at least one compound of Formula (I), or a pharmaceutically acceptable salt, ester, or prodrug thereof, in combination with a pharmaceutically acceptable carrier or excipient may be used for treating a subject with immune-mediated organ or tissue allograft rejection, a graft-versus-host disease, an autoimmune disease, an obstructive airway disease, a hyperproliferative disease, or an ischemic or inflammatory intestinal or bowel disease.

The present invention also relates to method(s) of treatment of immune disorders and inflammation or prevention of organ transplant rejection in a subject by administering to the subject therapeutically effective amounts of the cyclosporin analogs of Formula (I) with or without the concurrent use of other drugs or pharmaceutically acceptable excipients, as described throughout the present specification.

The methods of the present invention comprise treating a subject in need of immunosuppresive, anti-inflammatory, antimicrobial, antifungal, antiviral or antiproliferative therapy, or requiring the reversal of chemotherapeutic drug resistance, by administering a therapeutically effective amount of a compound of the invention for such time and in such amounts as is necessary to produce the desired result.

As used in the present invention, "therapeutically effective amount" of one of the compounds means a sufficient amount of the compound to treat a particular disease, at a reasonable benefit/risk ratio. The compounds of the present invention may be employed in pure form or, where such forms exist, in pharmaceutically acceptable salt, ester or prodrug forms. Alternatively, the compounds may be administered as pharmaceutical compositions containing the compound of interest in combination with one or more drugs or pharmaceutically acceptable excipients. It will be understood, however, that the total daily usage of the compounds and compositions of the present invention will be decided by the attending physician within the scope of sound medical judgment.

The specific therapeutically-effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 10 mg/kg of a patient's body mass/day. For purposes of oral administration, more preferable doses may be in the range of from about 0.005 to about 3 mg/kg/day. If desired, the effective daily dose may be divided into multiple doses for purposes of administration; consequently, single dose compositions may contain such amounts or submultiples thereof to make up the daily dose.

DEFINITIONS

The terms "$C_1$–$C_3$-alkyl" or "$C_1$–$C_6$-alkyl" as used herein refer to saturated, straight- or branched-chain hydrocarbon radicals containing between one and three or one and six carbon atoms, respectively. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "$C_1$–$C_6$-alkoxy" as used herein refers to an $C_1$–$C_6$-alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_6$-alkylthio" as used herein refers to an $C_1$–$C_6$-alkyl group, as previously defined, attached to the parent molecular moiety through a sulfur atom. Examples of $C_1$–$C_6$-alkylthio include, but are not limited to, thiomethoxy, thioethoxy, thiopropoxy, thio-isopropoxy, n-thiobutoxy, tert-thiobutoxy, neothiopentoxy and n-thio-hexoxy.

The term "aryl" as used herein refers to a carbocyclic ring system having one or more aromatic rings including, but not limited to, phenyl, naphthyl, tetrahydronaphthyl, indanyl, indenyl and the like. Aryl groups (including multi-cyclic aryl groups) can be unsubstituted or substituted with one, two or three substituents independently selected from lower alkyl, substituted loweralkyl, haloalkyl, alkoxy, thioalkoxy, lower alkylenedioxy, lower alkylidenedioxy, amino, alkylamino, dialkylamino, acyamino, cyano, hydroxy, acyl, halo and/or trifluoromethyl, mercapto, nitro, carboxylaldehyde, carboxy, alkoxycarbonyl, carbamoyl, sulfamoyl, lower alkoxycarbonylamino, lower alkanoyl, ureido, amidino and carboxamide. In addition, substituted aryl groups include tetrafluorophenyl and pentafluorophenyl.

The term "$C_3$–$C_6$-cycloalkyl-" as used herein refers to carbocyclic groups of 3 to 6 carbons, respectively; for example, cyclopropyl, cyclobutyl, cyclopentyl and cyclohexyl.

The terms "halo" and "halogen" as used herein refer to an atom selected from fluorine, chlorine, bromine and iodine.

The term "heterocyclics", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "subject" as used herein refers to a mammal or animal. Preferably the mammal is a human. A subject refers to, for example, dogs, cats, horses, cows, pigs, guinea pigs and the like.

The term "pro-drug" as used herein refers to pharmacologically acceptable derivatives, for example, but not limited to, esters and amides, such that the resulting biotransformation product of the derivative is the active drug. Pro-drugs are known in the art and are described generally in, e.g., Goodman and Gilman's "Biotransformation of Drugs," in the Pharmacological Basis of Therapeutics, 8$^{th}$ Ed., McGraw Hill, Int. Ed. 1992, page 13–15, which is hereby incorporated by reference in its entirety.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, but are not limited to, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyates, acrylates and ethylsuccinates.

Pharmaceutical Compositions

In the pharmaceutical compositions of the present invention, a compound of the invention is combined with a pharmaceutically acceptable carrier or excipient, meaning a non-toxic solid, semi-solid or liquid filler, diluent, encapsulating material or Formulation auxiliary of any type. The compositions may be administered orally, rectally, parenterally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions may contain, in addition to the active compounds, suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition are preferably such that the active ingredient does not dissolve therein to any substantial extent. The pressurized composition may also contain a surface-active agent, such as a liquid or solid non-ionic surface-active agent or may be a solid anionic surface-active agent. It is preferred to use the solid anionic surface-active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of Formula (I) may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of Formula (I), stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Abbreviations

| | |
|---|---|
| Sar: | Sarcosine |
| MeLeu: | N-Methyl-Leucine |
| Val: | Valine |
| Ala: | Alanine |
| MeVal: | N-Methyl Valine |
| Et: | Ethyl |
| Ph: | Phenyl |
| Fmoc: | 9-Fluorenylmethoxycarbonyl- |
| MeBmt: | N-Methyl-(4R)-4-[(E)-2-butenyl]-4-methyl-L-threonine |
| α-Abu: | α-Aminobutyric acid |

Synthetic Methods

The compounds used in the present invention will be better understood, but are not limited to, the following synthetic scheme which illustrates the methods by which the compounds of Formula I may be prepared. The groups X and Y, and the amino acid residues B and U in Formula I are as defined earlier in the specification. The starting material for Scheme I, illustrated by Formula I where A'=-MeBmt-, may be, for example, but not limited to, a fermentation product or a synthetic product made by solution phase chemistry. Preferably, the starting material is commercially available. The starting material as a fermentation product may be made from highly productive strains, for example, but not limited to, *Sesquicillopsis rosariensis* G. ARNOLD F605; *Tolypocladium inflatum* wb6-5; Fusant, *Tolypocladium inflatum* KD461 etc. (in U.S. Pat. Nos. 5,256,547; 5,856,141 etc.). Alternately, the starting material may be made by solution phase chemistry either by sequentially assembling amino acids or by linking suitable small peptide fragments, where the units are linked by, for example, but not limited to, amide, ester or hydroxylamine linkages (described in, *Müller, Methoden der organischen*, Chemie Vol. XV/2, pp 1 to 364, Thieme Verlag, Stuttgart, 1974; Stewart, Young, Solid Phase Peptide Synthesis, pp 31 to 34, 71 to 82, Pierce Chemical Company, Rockford, 1984; Bodanszky, Klausner, Ondetti, Peptide Synthesis, pp 85 to 128, John Wiley & Sons, New York, 1976 and other standard books on solution phase peptide chemistry). For amide linkages particular preference is given to the azide method, the symmetric and mixed anhydride method, in situ generated or preformed active esters and methods using coupling reagents (e.g., dicyclohexylcarbodiimide, N,N-dimethyl-4-aminopyridine, N-hydroxy-benzotriazole, PyBrop® etc.). Classical solution phase chemistry using standard Z- and Boc-methodology may be used.

Residue A, which is -MeBmt- in the starting material is further modified, as illustrated in the following reaction scheme.

Scheme:

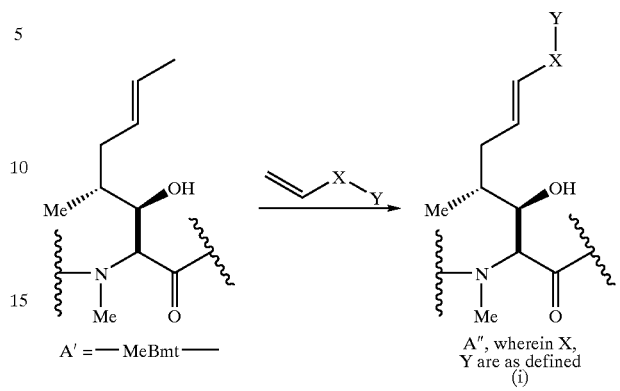

The process for preparing compounds of Formula I comprises reacting a compound of Formula I wherein A=-MeBmt- (cyclosporin A, commercially available fermentation product) with an olefin having a terminal double bond with Grubb's ruthenium alkylidene or benzylidene catalysts [see (a) U.S. Pat. No. 6,111,121; (b) Reviews: Synlett, 1999, 2, 267; (c) Reviews: Ivin, K J; Mol, J. C. *Olefin Metathesis and Metathesis Polymerization*, 2$^{nd}$ ed, Academic Press, New York, 1997; (d) *J. Org. Chem.*, 1999, 64, 4798–4816; (e) *Angew. Chem.*, Int. Ed. English, 1997, 36, 2036–2056; (f) *Tetrahedron* 1998, 54, 4413–4450.] or Nolan's ruthenium catalyst [see (a) International Patent Application No. WO 00/15339; (b) *Org. Lett.*, 2000, 2, 1517–1519; (c) *J. Org. Chem.*, 2000, 65, 2204–2207] or Molybdenum catalysts [see (a) *J. Am. Chem. Soc.*, 1990, 112, 3875 (b), *J. Am. Chem. Soc.*, 1996, 118, 10926–10927] in the presence of a lithium salt in an organic solvent such as dichloromethane, chloroform, toluene, benzene, tetrahydrofuran, dimethylformamide, and the like at from room temperature to about 100° C. for 1–7 days to provide a compound of Formula I.

EXAMPLES

The procedures described above for preparing the compounds of Formula (I) used in the present invention will be better understood in connection with the following examples, which are intended to be illustrative only and not limiting of the scope of the invention. Various changes and modifications of the disclosed embodiments will be apparent to those skilled in the art. Such changes and modifications, including without limitation, those relating to the chemical structures, substituents, derivatives, intermediates, syntheses, formulations and/or methods for the invention may be made without departing from the spirit of the invention and the scope of the appended claims.

Example 1

Compound of Formula (I): B is -αAbu-, U is -(D)Ala-, X is Absent, Y=COOCH3

Methyl acrylate (0.037 ml, 0.42 mmol), lithium bromide (0.014 g, 0.218 mmol), and 1,3-bis(2,4,6-trimethylphenyl)

imidazol-2-ylinene(tricyclohexylphosphine)dichloro ruthenium(II) bexylidene (Nolan catalyst, 0.0071 g, 0.008 mmol) were added to a solution of cyclosporin A (0.1 g, 0.084 mmol) in methylene chloride/tetrahydrofuran (10:1, 3 ml) at room temperature. The reaction mixture was heated at 40° C. After 24 hours, more Nolan catalyst (0.0071 g, 0.008 mmol) and methyl acrylate (0.037 ml, 0.42 mmol) in 10:1 methylene chloride/tetrahydrofuran (3 ml) were added and heated at 40° C. for additional 24 hours. After being cooled to room temperature, the reaction mixture was filtered through a pre-packed solid phase extraction cartridge and then eluted with 40:1 to 20:1, by volume, methylene chloride/methanol. Removal of solvent in vacuo gave the title compound as a brownish solid.

MS (ESI) m/z 1245.78 $(M+H)^+$.

Example 2

Compound of Formula (I): B is -αAbu-, U is -(D)Ala-, X is Absent, Y=COOH

The title compound of Example 2 was prepared from the title compound of Example 1, reacted with sodium hydroxide in aqueous methanol.

MS (ESI) m/z 1232.82 $(M+H)^+$.

Example 3

Compound of Formula (I): B is -αAbu-, U is -(D)Ala-, X is Absent, Y=COOEt

The title compound of Example 3 was prepared from cyclosporin A, ethyl acrylate, Nolan catalyst and LiBr according to the procedures described in Example 1.

MS (ESI) m/z 1245.78 $(M+H)^+$.

Example 4

Compound of Formula (I): B is -αAbu-, U is -(D)Ala-, X is Absent, Y=COOCH$_2$CH$_2$CH$_3$ The title compound of Example 4 was prepared from cyclosporin A, n-propyl acrylate, Nolan catalyst and LiBr according to the procedures described in Example 1.

MS (ESI) m/z 1280.45 $(M+H)^+$.

Example 5

Compound of Formula (I): B is -αAbu-, U is -(D)Ala-, X is Absent, Y=COOCH$_2$Ph

The title compound of Example. 5 was prepared from cyclosporin A, benzyl acrylate, Nolan catalyst and LiBr according to the procedures described in Example 1.

MS (ESI) m/z 1322.86 $(M+H)^+$.

Example 6

Compound of Formula (I): B is -αAbu-, U is -(D)Ala-, X is Absent, Y=COOCH$_2$F

The title compound of Example 6 is prepared from cyclosporin A, fluoromethyl acrylate, Nolan catalyst and LiBr according to the procedures described in Example 1.

Example 7

Compound of Formula (I): B is -αAbu-, U is -(D)Ala-, X is Absent, Y=COOCHF$_2$

The title compound of Example 7 is prepared from cyclosporin A, difluoromethyl acrylate, Nolan catalyst and LiBr according to the procedures described in Example 1.

Example 8

Compound of Formula (I): B is -αAbu-, U is -(D)Ala-, X is Absent, Y=COOCF$_3$

The title compound of Example 8 is prepared from cyclosporin A, trifluoromethyl acrylate, Nolan catalyst and LiBr according to the procedures described in Example 1.

Example 9

Compound of Formula (I), B is -αAbu-, U is -(D)Ala-, X is Absent, Y=COOCH$_2$CF$_3$ The title compound of Example 9 is prepared from cyclosporin A, trifluoroethyl acrylate, Nolan catalyst and LiBr according to the procedures described in Example 1.

Example 10

Compound of Formula (I): B is -αAbu-, U is -(D)Ala-, X is Absent, Y=COOCH$_2$Cl

The title compound of Example 10 is prepared from cyclosporin A, chloromethyl acrylate, Nolan catalyst and LiBr according to the procedures described in Example 1.

Example 11

Compound of Formula (I): B is -αAbu-, U is -(D)Ala-, X is Absent, Y=COOCH$_2$OCH$_3$ Method A.

The title compound of Example 11 is prepared from cyclosporin A, methoxymethyl acrylate, Nolan catalyst and LiBr according to the procedures described in Example 1.

Method B.

The title compound of Example 11 is prepared from the title compound of Example 2, triethylamine and methyoxymethyl chloride in DMF according to the procedures described in Protective Groups in Organic Synthesis, 3 rd Ed, T. W. Greene and P. G. M. Wuts ed., John Wiley & Sons, Inc, 1999.

Example 12

Compound of Formula (I): B is -αAbu-, U is -(D)Ala-, X is Absent, Y=COOCH$_2$OCH$_2$CH$_2$O CH$_3$ Method A.

The title compound of Example 12 is prepared from cyclosporin A, methoxyethoxymethyl acrylate, Nolan catalyst and LiBr according to the procedures described in Example 1.

Method B.

The title compound of Example 12 is prepared from the potassium salt of the title compound of Example 2, methoxyethoxymethyl chloride, Hunig's base in methylene chloride according to the method described in Protective Groups in Organic Synthesis, op. cit.

Example 13

Compound of Formula (I): B is -αAbu-, U is -(D)Ala-, X is Absent, Y=C(=O)SCH$_2$Ph The title compound of Example 13 is prepared from the title compound of Example 2, benzyl mercaptan, carbodiimide and dimethylaminopyridine in methylene chloride according to the method described in Protective Groups in Organic Synthesis, op. cit.

Example 14

Compound of Formula (I): B is -αAbu-, U is -(D)Ala-, X is —CH$_2$CH$_2$CH$_2$—, Y=COOCH$_3$ The title compound of Example 14 was prepared from cyclosporin A, methyl 5-hexenoate, Nolan catalyst and LiBr according to the procedures described in Example 1.

MS (ESI) m/z 1287.08 (M+H)$^+$.

Example 15

Compound of Formula (I): B is -αAbu-, U is -(D)Ala-, X is Absent, Y=COOFmoc

The title compound of Example 15 was prepared from cyclosporin A, Fmoc acrylate, Nolan catalyst and LiBr according to the procedures described in Example 1.

MS (ESI) m/z 1410.89 (M+H)$^+$.

The immunosuppressive and anti-inflammatory properties of cyclosporin analogs of the invention may be demonstrated in standard test models in vitro and in vivo for example as follows.

Example 16

Calcineurin Inhibition Assay

The immunosuppressive activity of cyclosporin is mediated through inhibition of the phosphatase activity of the enzyme calcineurin by a cyclophilin-cyclosporin complex. Thus, calcineurin inhibition is widely used as an in vitro measure of the activity of cyclosporin analogs.

Compounds were tested in an assay based on the Biomol Green Calcineurin Assay Kit supplied by Biomol (Plymouth Meeting, Pa.), supplemented with cyclophilin A for enzyme inhibition. The activity of the recombinant human calcineurin was determined by release of phosphate from a phosphopeptide representing a fragment of camp-dependent protein kinase. Phosphate release was determined using the calorimetric detection reagent Biomol Green.

Compounds in DMSO (2.4 μl) were added to a 96-well microplate and mixed with 50 μl assay buffer (50 mM Tris, pH 7.5, 0.1 M sodium chloride, 6 mM magnesium chloride, 0.5 mM dithiothreitol, 0.025% NP-40, 0.5 mM calcium chloride, 0.25 μM calmodulin) containing 5 μM cyclophilin and 20 units of calcineurin. After warming to 37° C. for 15 min, the enzymatic reaction was initiated by addition of phosphopeptide (7.5 μl) to give a final concentration of 94 μM. Phosphate release after 60 min at 37° C. was determined by addition of Biomol Green (100 μl) and measurement of the absorbance at 620 nm after 15 min at room temperature.

IC$_{50}$ values were calculated from determinations of enzyme activity at inhibitor concentrations ranging from 20 to 0.006 μM.

Example 17

Immunosuppressive Activity and Applications

Murine Mixed Lymphocyte Reaction

Ca. 0.5×10$^6$ lymphocytes from the spleen of female (8–10 weeks) Balb/c mice are incubated for 5 days in 0.2 ml cell growth medium with ca. 0.5×10$^6$ lymphocytes from the spleen of female (8–10 weeks) CBA mice. Test substance is added to the medium at various concentrations. Activity is assessed by ability to suppress proliferation-associated DNA synthesis as determined by incorporation of radiolabelled thymidine.

Mishell-Dutton Test

Ca. 10$^7$ lymphocytes from the spleen of OFI, female mice are co-cultured with ca. 3×10$^7$ sheep erythrocytes for 3 days. Test substance is added to the incubation medium in varying concentrations. Lymphocytes are harvested and plated onto agar with fresh sheep erythrocytes as antigen. Sensitized lymphocytes secrete antibody that coats the erythrocytes, which lyse to form a plaque in the presence of complement. Activity is assessed by reduction in the number of plaque forming, i.e., antibody product, cells.

Influence on Allergen-Induced Pulmonary EosinoDhilia (in vitro)

Male Himalayan spotted guinea pigs (300 g, BRL) are sensitized to ovalbumin (OA) by i.p. injection of 1 ml of a suespension of OA (10 μg/ml) with Al(OH)$_3$(100 mg) and B-pertussis vaccine (0.25 ml) in saline (0.9% w/v). For oral studies the procedure is repeated 1× after 2 weeks and the animals are used one week later. For inhalation studies the procedure is repeated 2× at 3-week intervals and the animals are used one week after the last injection.

Challenge is effected employing a saline solution of OA, nebulized for discharge into an exposure chamber. Test animals are exposed to OA by nose-only inhalation for 60 minutes. For inhalation studies, OA solution is used at a concentration of 0.01%.

Test substance is administered (a) inhalation and/or (b) orally. For oral studies, test substance is administered p.o. in olive oil 1× daily for 3 days or in powder form in methylcellulose once prior to OA challenge. On day 3, test animals receive test substance 1.5 hrs. prior to and 6 hrs. after OA challenge. For inhalation studies, test substance is micronised for delivery to test animals restrained within a flow-past, nose-only inhalation chamber. Administration by inhalation is effected 15 mins. prior to OA challenge.

Efficacy of administered test substance is determined by bronchoalveolar lavage (BAL) and cell counting. For this purpose animals are sacrificed with Na pento-barbitone (100 mg/kg i.p.) and the trachea is exposed and cannulated. 5 successive 10 ml aliqots of $Ca^{2+}$ and $Mg^{2+}$ free Hank's balanced salt solution (HBSS), containing bovine serum albumin (BSA, 0.3%), EDTA (10 mM) and HEPES (10 mM) is then introduced into the lung and immediately aspirated by gentle compression of the lung tissue. Total cell counts in pooled eluates are determined using an automatic cell counter. Lavage fluid is centrifuged at 200 g for 10 minutes and the cell pellet resuspended in 1 ml of supplemented HBSS. 10 µl of this cell suspension is added to 190 µl of Turk's solution (1:20) dilution). Differential cell counts are made from smears stained by Diff-Quick. Cells are identified and counted under oil immersion (×1,000). A minimum of 500 cells per smear are counted and the total population of each cell type is calculated.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A method of treating an inflammatory or immune disorder in a subject while reducing the toxicity associated with the administration of cyclosporin A, comprising systemically administering to said subject a pharmaceutical composition comprising a therapeutically effective amount of at least one compound of Formula (I) or a pharmaceutically acceptable salt, ester or prodrug thereof, in combination with a pharmaceutically acceptable carrier or excipient:

(I)

```
┌─A---B---Sar-MeLeu-Val-MeLeu-Ala---U---MeLeu-MeLeu-MeVal─┐
│ 1   2                          8                        │
``` wherein A is:

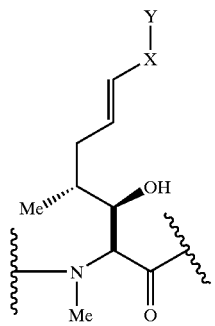

X is absent, —$C_1$–$C_6$ alkyl-, or —$C_3$–$C_6$ cycloalkyl

Y is selected from the group consisting of:

(i) C(O)—O—$R^1$, where $R^1$ is hydrogen, $C_1$–$C_6$ alkyl, optionally substituted with halogen, heterocyclic, aryl, $C_1$–$C_6$-alkoxy, $C_1$–$C_6$ alkylthio, halogen-substituted $C_1$–$C_6$ alkoxy, or halogen-substituted $C_1$–$C_6$ alkylthio;

(ii) C(O)—S—$R^1$, where $R^1$ is as previously defined;

(iii) C(O)—$OCH_2$—$OC(O)R^2$, where $R^2$ is $C_1$–$C_6$ alkyl, optionally substituted with halogen, $C_1$–$C_6$ alkoxy, $C_1$–$C_6$ alkylthio, heterocyclic or aryl;

(iv) C(S)—O—$R^1$, where $R^1$ is as previously defined, and (v) C(S)—S—$R^1$, where $R^1$ is as previously defined;

B is -αAbu-, -Val-, -Thr- or -Nva-; and

U is -(D)Ala-, -(D)Ser-, —[O-(2-hydroxyethyl)(D)Ser]-, —[O-acyl(D)Ser]- or —[O-(2-acyloxyethyl)(D)Ser]-.

2. The method of claim 1, wherein said inflammatory or immune disorder is organ transplant rejection.

3. The method of claim 1, wherein said inflammatory or immune disorder is selected from the group consisting of: rheumatoid arthritis, inflammatory bowel disease, psoriasis, atopic dermatitis, asthma, allergic rhinitis, and chronic obstructive pulmonary disease.

4. The method of claim 1, wherein said systemically administering is accomplished orally, intraperitoneally, intravenously, intramuscularly, intrasternally, subcutaneously, or through intravenous injection or infusion.

* * * * *